(12) United States Patent
Campbell et al.

(10) Patent No.: US 6,358,240 B1
(45) Date of Patent: *Mar. 19, 2002

(54) LOW PROFILE FLEXIBLE PUSHER ROTATOR

(75) Inventors: Louis A. Campbell; Jeffrey M. Mabrey; Christopher A. Heinrich, all of Austin, TX (US)

(73) Assignee: Sulzer Carbomedics Inc., Austin, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/340,251

(22) Filed: Jul. 1, 1999

Related U.S. Application Data

(63) Continuation-in-part of application No. 08/851,572, filed on May 5, 1997, now Pat. No. 5,957,709.

(51) Int. Cl.[7] .............................................. A61B 17/00
(52) U.S. Cl. ........................ 606/1; 623/2.11; 623/66.1; 606/108
(58) Field of Search ................................ 623/2.11, 2.1, 623/66.1, 900; 606/1, 108, 99

(56) References Cited

U.S. PATENT DOCUMENTS

| | | | | |
|---|---|---|---|---|
| 5,403,305 A | * | 4/1995 | Sauter et al. ................... 606/1 |
| 5,480,425 A | | 1/1996 | Ogilive ........................... 623/2 |
| 5,571,215 A | | 11/1996 | Sterman et al. ................ 623/66 |
| 5,578,076 A | | 11/1996 | Krueger et al. ................. 623/2 |
| 5,713,951 A | | 2/1998 | Garrison et al. ................ 623/2 |
| 5,713,952 A | | 2/1998 | Vanney et al. .................. 623/2 |
| 5,776,187 A | * | 7/1998 | Krueger et al. ................. 623/2 |
| 5,876,437 A | | 3/1999 | Vanney et al. .................. 623/2 |
| 5,954,709 A | * | 9/1999 | Campbell et al. .............. 606/1 |
| 6,090,138 A | * | 7/2000 | Chasak et al. ................. 623/2 |

* cited by examiner

*Primary Examiner*—Linda C. M. Dvorak
*Assistant Examiner*—Jocelyn Debra Ram
(74) *Attorney, Agent, or Firm*—Philip S. Lyren; Timothy L. Scott

(57) ABSTRACT

A device for releasably holding and positioning a heart valve prosthesis includes a handle having a first end, a second end and a super elastic shaft interconnecting the first and second ends. A connector is positioned at the second end of the handle and includes a plug portion having a pair of raised members and diametrically opposed guide slots. A low profile pusher-rotator is releasably engaged with the plug portion and includes diametrically opposed guide tabs engaged with the guide slots. A manually flexible release portion of the pusher-rotator includes a pair of engagement members engaged in a snap fit with the raised members. The release portion can be manually distorted to release the engagement members and the raised members for separation of the handle and the pusher-rotator.

23 Claims, 9 Drawing Sheets

LOW PROFILE FLEXIBLE PUSHER ROTATOR

This is a continuation-in-part of application Ser. No. 08/851,572 filed May 5, 1997, now U.S. Pat. No. 5,957,709 issued Sep. 21, 1999. The disclosures herein relate generally to heart valve replacement and more particularly to a low profile flexible pusher rotator for positioning a prosthetic heart valve during implantation.

BACKGROUND

Some heart valve replacement surgeries rely on a median sternotomy or a large right thoracotomy to allow unobstructed access for introducing the heart valve prosthesis into the native valve's annulus and for subsequent rotation of the orifice and leaflets assembly to minimize potential leaflet interference with sub-annular anatomy.

The median sternotomy or a large left thoracotomy, to gain unobstructed access into a patient's thoratic cavity, allows the surgeon to see the patient's heart more directly, and to have more direct instrument access for: (1) excising the natural valve tissue; (2) introducing a heart valve prosthesis into the patient's natural valve annulus; (3) securing the prosthetic valve into position; and (4) rotating the orifice and leaflet assembly of the prosthesis to minimize interference with the heart's subannular anatomy. However, these invasive, open-chest procedures produce a high degree of trauma, a significant risk of complications, extended hospital stay, and a painful recovery period for the patient.

Recently developing Less Invasive Surgery (LIS) techniques rely on a small intercostal thoracotomy instead of a median sternotomy or large thoracotomy to gain access to the thoracic cavity. The small intercostal thoracotomy substantially reduces the above-mentioned trauma, risk of complication, recovery time, and pain for the patient. Experience indicates the thoracotomy incision should not be spread greater than 15 mm for an intercostal insertion because deflecting the ribs to a greater dimension can result in significant pain for the patient as the nerve under the rib can be crushed and damaged.

In known related technology, a trocar, approximately 20 mm wide, is positioned in an intercostal space requiring some deflection of the ribs. A disposable low profile valve holder used with a disposable handle/introducer provides the ability to pass a heart valve prosthesis sideways through the trocar and then pivoted 90 degrees to be introduced into the mitral valve's annulus. The handle/introducer and valve holder therefore offers no utility beyond the use of a standard endoscopic articulating mechanism attached to a currently available holder or rotator. Currently marketed handles and valve holders are used for the valve introduction, and subsequent rotation is executed with currently marketed rotators or valve holders designed to rotate the valve.

Therefore, the devices and instruments for performing percutaneous penetrations within these intercostal spaces for less-invasive heart or great vessel surgery must be simple and have a "low profile". Currently marketed rotators and valve holders are too bulky to fit through this intercostal space without spreading the patient's ribs too far, and are more complicated than necessary to simply and reliably percutaneously introduce and rotate a prosthetic valve during implantation.

Mechanical heart valve prostheses include valves having one, two or more rigid leaflets. One popular valve design for a mechanical heart valve prosthesis includes an annular valve body in which a pair of opposed leaflet occluders are pivotally mounted. The occluders are movable between a closed, mated position, blocking blood flow in an upstream direction and minimizing regurgitation, and an open position, allowing blood flow in a downstream direction. The annular valve body is surrounded by a sewing ring which permits the surgeon to suture the valve in place at the site of an excised valve.

When a valve is placed within the heart, it must be accurately oriented to maximize its function. Particularly in mechanical heart valves, the orientation of the leaflets is critical since their opening and closing pathways may otherwise impinge on the surrounding cardiac walls, the walls of arteries within which the valve is placed, or the residual valvular structures including the tendeae chordae and papillary muscles. This difficulty becomes particularly acute in the placement of a heart valve in the position of the mitral valve in the heart. When replacing this valve, a surgeon will frequently expose the posterior side of the patient's heart and enter the heart through the wall of the left atrium and sometimes through the right atrium. It is desirable to place the valve accurately within the cramped confines of the heart while leaving room for the surgeon to sew the valve in place.

To aid in the rotation of the heart valve within a sewing ring, heart valve prosthesis rotators have been proposed heretofore. Some of these rotators have bendable metal shafts which can be bent by the surgeon interoperatively, but which will retain their bent shape, requiring significant space for proper manipulation of a heart valve engaged by the rotator. The shafts of some of these rotators are constructed of a shape-memory alloy, which construction allows the shaft to recover its original straight shape upon sterilization. The term "shape-memory alloys" refers to that group of metallic materials that demonstrate the ability to return to same previously defined shape and size when subjected to the appropriate thermal procedure. These materials can be plastically deformed at some relatively low temperature, and upon exposure to higher temperatures, will return their shape prior to the deformation. Rotators containing shape-memory alloy shafts can be easily positioned by bending the shaft to the desired orientation. To return the shaft to its original shape, the shaft is heated (i.e., during the sterilization process) to a temperature above the alloy's transformation temperature.

With the increased use of less invasive cardiac surgical procedures a rotator is needed that can turn a heart valve within a very limited space. To accomplish this, a rotator must have both flexibility and torqueability (i.e., kink resistance). The rotator must have the ability to absorb large amounts of strain energy and release it as the applied strain is released.

A recent low profile mechanical valve introducer and rotator is composed of a series of coaxial cylinders which are truncated resulting in a width of 14 mm. There is also a central slot to provide clearance for the leaflets after engaging a heart valve prosthesis. The outermost cylinder acts as a stop for the introducer/rotator when it contacts the inflow edge of the orifice, therefore, limiting the application of significant load to the leaflets. The intermediate cylinder, which induces the rotation of the orifice and leaflets assembly, has an additional truncation occurring 90 degrees from the first that matches with the orifice's internal diameter flat. Also, proximal to this truncation is a notch that helps guide the introducer/rotator into the correct alignment for full engagement into the orifice and leaflets assembly when presented at an angle to the assembly's central axis. The intermost cylinder allows the introducer/rotator to rotate freely on the leaflets' inflow edge which helps to guide the introducer/rotator into the correct rotational alignment for full engagement into the orifice and leaflets assembly.

This embodiment can be passed through an incision of less than 15 mm in width. It can then be used to engage a heart valve prosthesis (that has been previously positioned or "button holed" into the thoracic cavity) to introduce the prosthesis into the annulus. It can also be used to rotate the orifice and leaflets assembly to the optimum orientation after the tails of the sutures used to secure the valve are tied off. Currently marketed handles and valve holders cannot pass through a 15 mm wide incision to introduce and rotate the heart valve prosthesis. A recently developed heart valve prosthesis rotator has a flexible drive shaft. In use, the drive shaft can be bent to a desired direction but will transmit torque to a heart valve rotator head, orienting a prosthetic heart valve mounted thereon. Moreover, the shaft will return to its original shape after force is removed. The shaft may be constructed of material such as super-elastic nickel-titanium alloy, which allows the rotator to be easily sterilized for re-use.

In another embodiment, the heart valve prosthesis rotator also has an annealed stainless steel shaft which can be bent by the surgeon interoperatively. The shaft will retain its shape after bending. Surrounding the shaft we have provided a drive coil which connects a rotator head at a proximal end of the shaft to a drive knob at a distal end of the shaft and adjacent a handle. By turning the drive knob, a surgeon can turn the rotator head, thus orienting the prosthetic heart valve. Torsional motion is carried along the path defined by the bendable shaft so that the rotator head can be turned without displacing the handle of the heart valve rotator.

Therefore, what is needed is a flexible handle which can be releasably attached to the low profile introducer rotator for pushing and rotating the prosthetic heart valve into position.

SUMMARY

One embodiment, accordingly, discloses a combination low-profile pusher-rotator releasably attachable to a flexible handle for easy insertion between adjacent ribs for proper positioning of a heart valve prosthesis with a natural valve annulus. To this end, a device for releasably holding and positioning a heart valve prosthesis includes a handle having a first end, a second end and a super elastic shaft interconnecting the first end with the second end. A connector is at the second end of the handle and includes a connector portion. A low profile pusher rotator is releasably engaged with the connector portion and includes a manually flexible release portion having engagement surfaces engaged with the connector portion.

A principal advantage of this embodiment is that attachment of the handle and the pusher-rotator is accomplished by a snap-on engagement and is also provided for quick release. The device easily engages a reusable endoscopic instrument, avoiding costly disposable valve handles such as those presently in use. The pusher-rotator easily passes through the common size 15 mm wide percutaneous intercostal incision avoiding the need to spread adjacent ribs apart. Parts are either machined or injection molded out of materials suited to the biomedical industry. Also, the device permits ease of engagement with a heart valve prosthesis for introduction into a natural valve annulus and subsequent rotation of the heart valve prosthesis for alignment of the valve orifice and leaflets without imposing damage on the leaflets.

BRIEF DESCRIPTION OF THE DRAWING FIGURES

Figures 6, 6A:
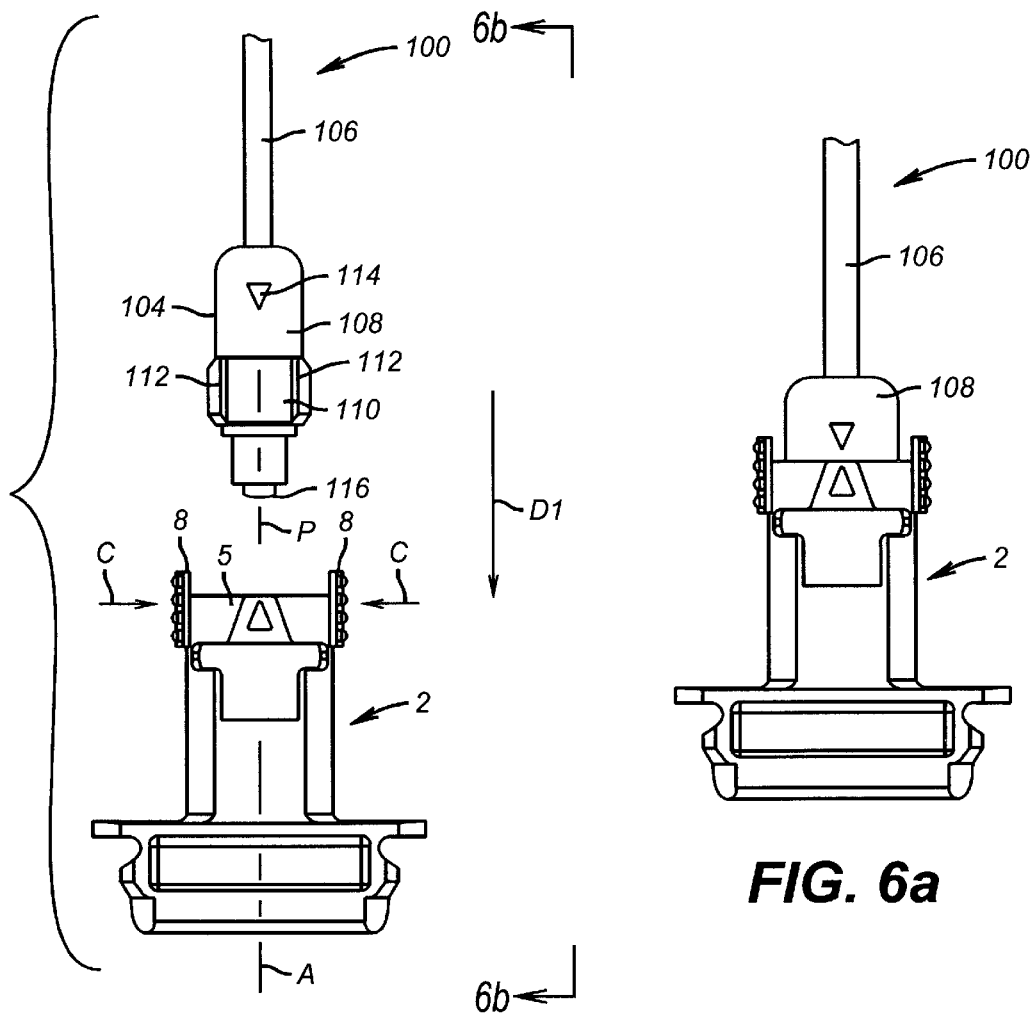
FIG. 6 is a side view partially illustrating an embodiment of an end of a handle disconnected from a pusher-rotator.

FIG. 6*a* is a side view illustrating an embodiment of an end of a handle connected to the pusher-rotator.

Figure 6B:
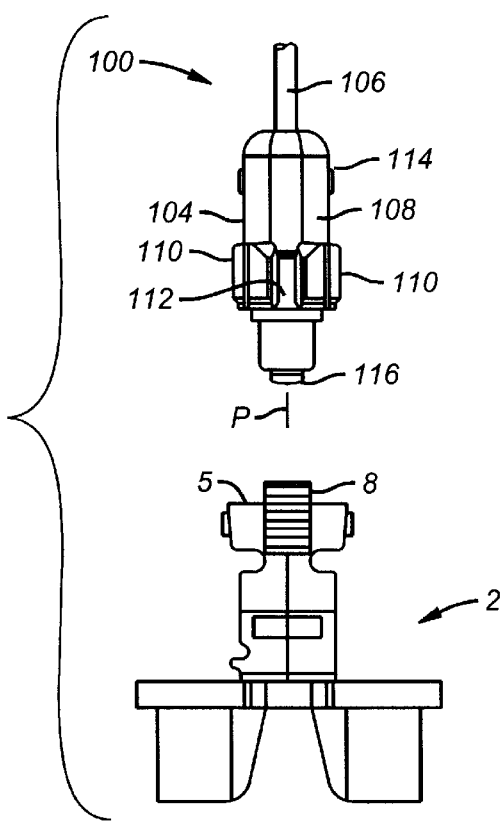

FIG. 6*b* is another side view illustrating an embodiment of a handle disconnected from a pusher rotator as viewed from the line 6*b*—6*b* of FIG. 6.

Figure 7:
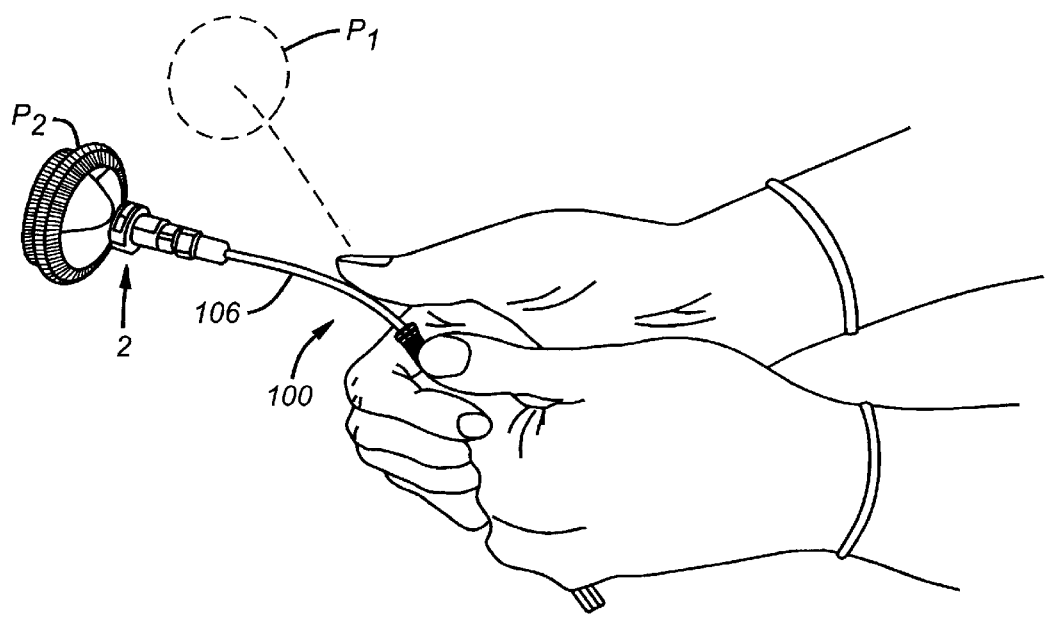

FIG. 7 is an isometric view illustrating an embodiment of a handle and pusher-rotator engaged with a heart valve prosthesis.

Figure 8:
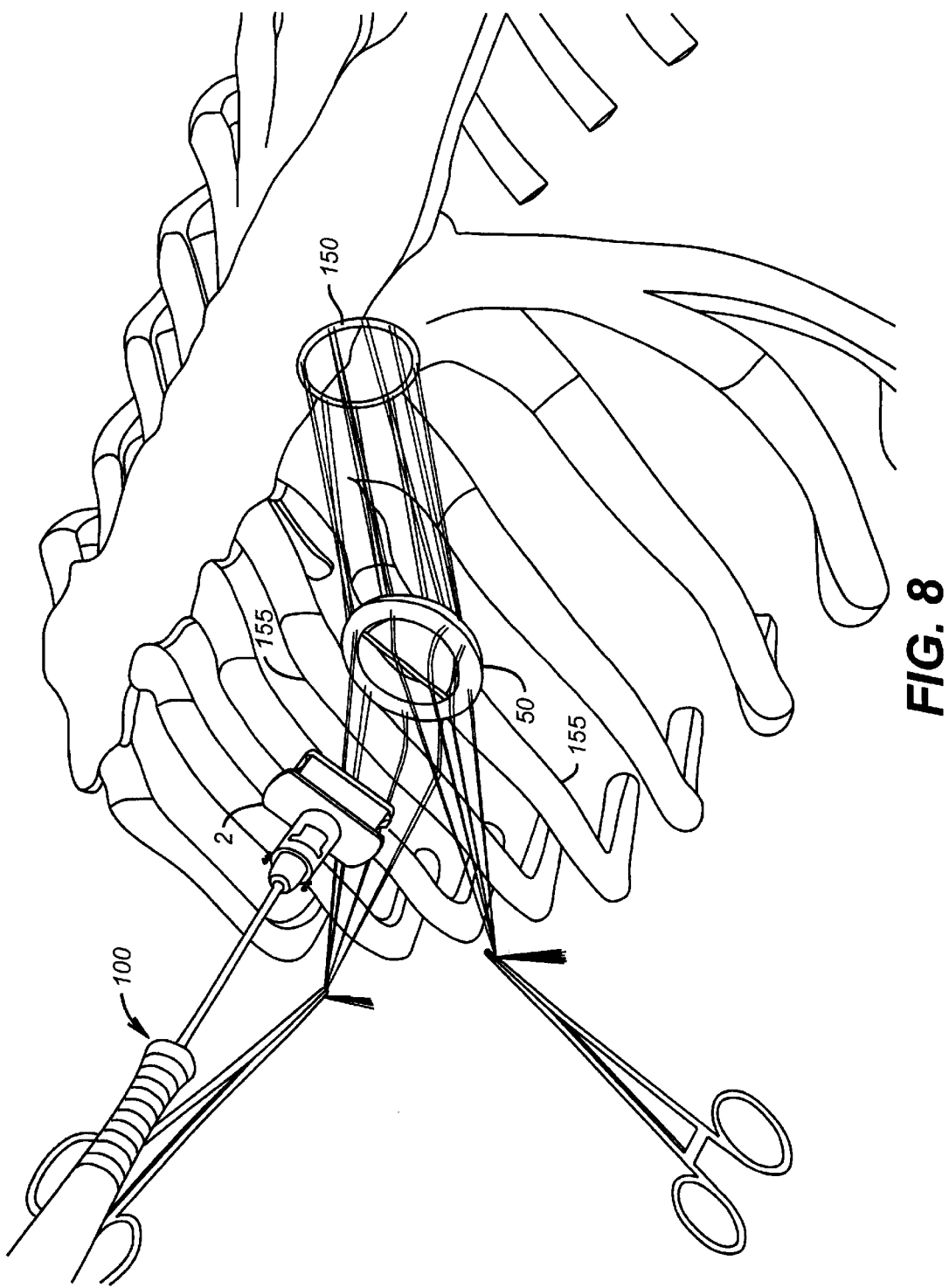

FIG. 8 is an isometric view illustrating an embodiment of a handle and pusher-rotator positioned for insertion between adjacent ribs to engage a heart valve prosthesis.

Figure 9:
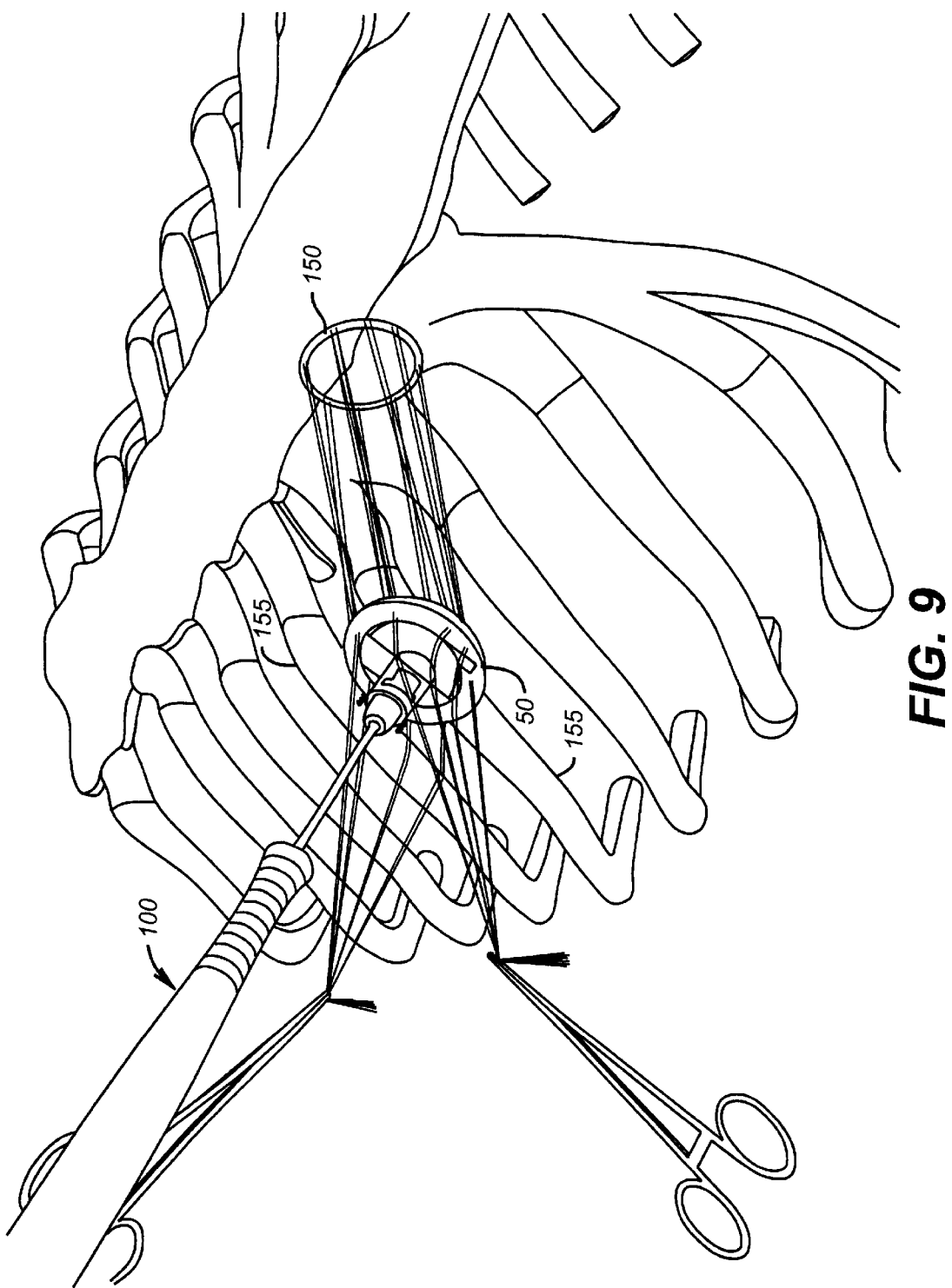

FIG. 9 is an isometric view illustrating an embodiment of a handle and pusher-rotator inserted between adjacent ribs and engaged with a heart valve prosthesis.

Figure 10:
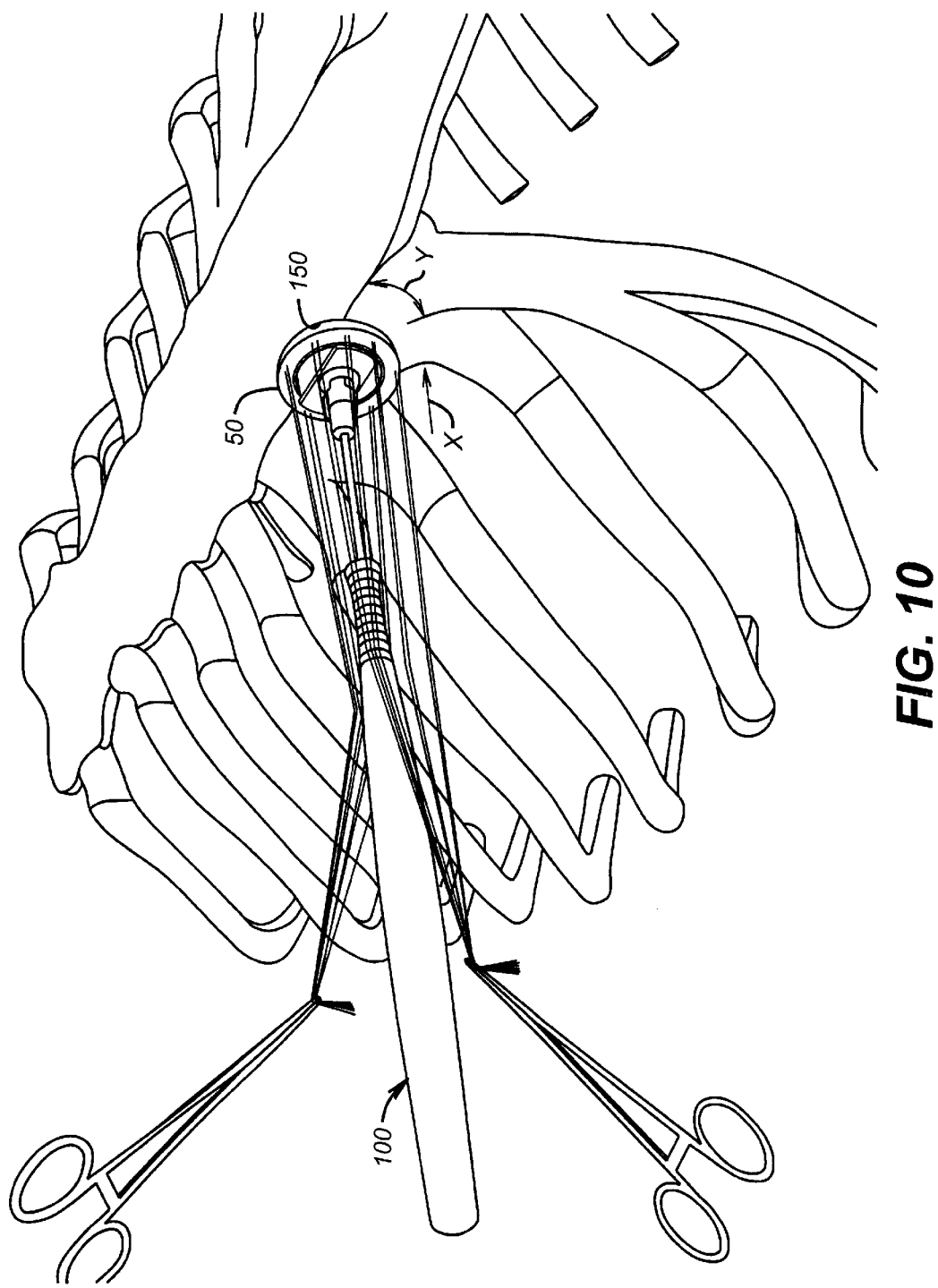

FIG. 10 is an isometric view illustrating an embodiment of a handle and pusher-rotator inserted between adjacent ribs, pushing and rotating a sutured heart valve into a natural valve annulus.

DETAILED DESCRIPTION

Referring to FIGS. 1–4, a prosthetic valve pusher-rotator 2 includes a handle engaging end 4 which is designed to be releasably connected to the shaft of a handle (discussed below). An alignment indicator 6 marks the position for the user to introduce the handle into engaging end 4. Pusher-rotator 2 includes a longitudal axis designated A. A similar indicator exists on a connector end of the handle (discussed below), so that the user simply lines up the indicators in order to put the instrument together. In this particular embodiment, a pair of finger tabs 8 are provided to release the handle from engaging end 4. Engaging end 4 provides a snap fit with the connector end of the handle (discussed below), with the tip of the connector end of the handle resting in an engagement recess 10 when the handle and pusher-rotator 2 are connected. Engagement recess 10 is shown as a smooth recess so that the connector end of the handle slip-fits into recess 10. Also provided in the engaging end 4 are a pair of diametrically opposed self-guiding tabs 12 which axially extend and allow the connector end of the handle to be correctly positioned for coupling with pusher-rotator 2.

Figure 2:
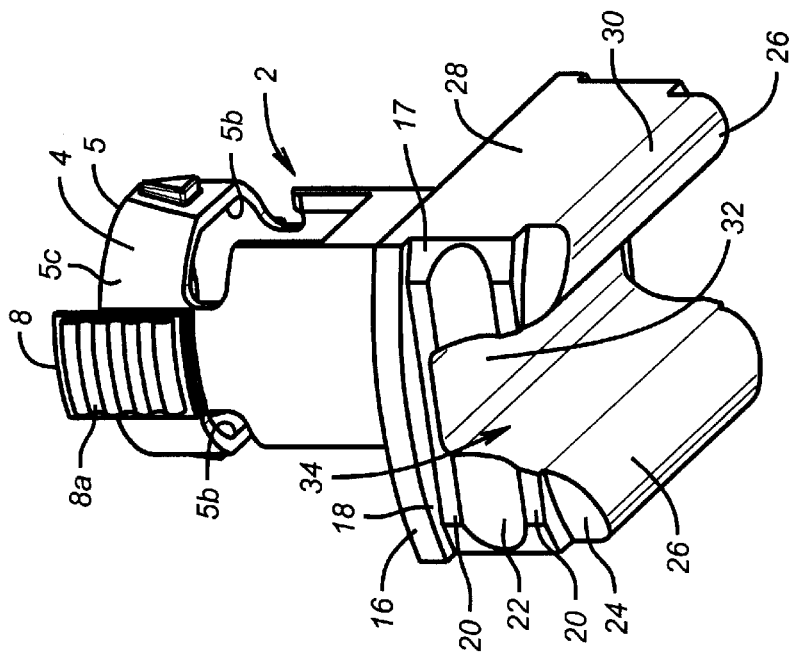
FIG. 2 is another isometric view of the pusher-rotator of FIG. 1.
Figure 1:
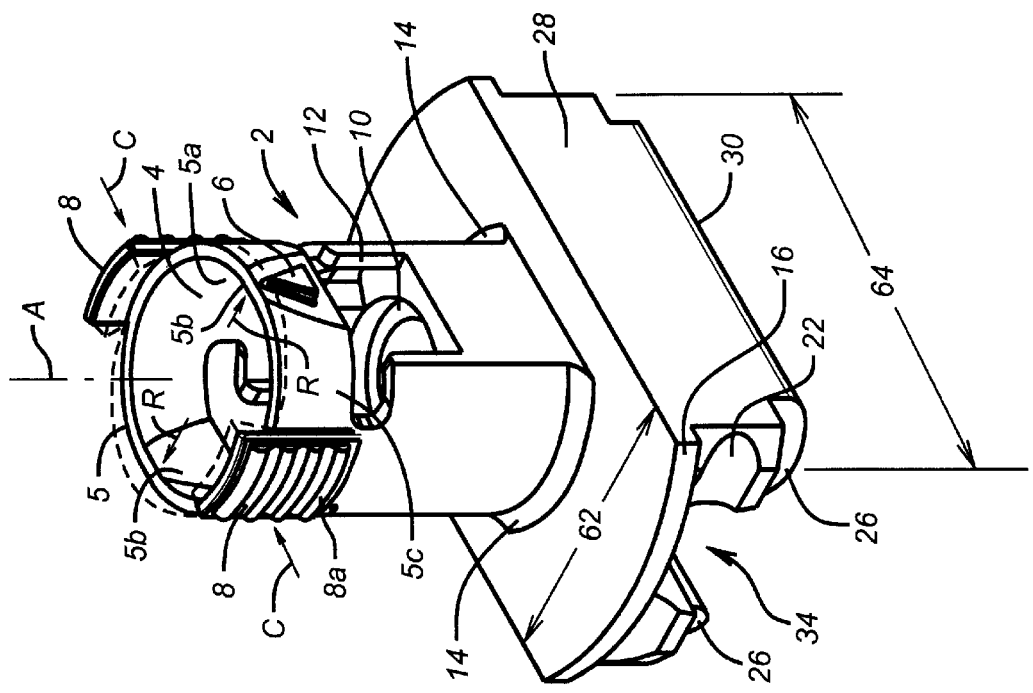
FIG. 1 is an isometric view illustrating an embodiment of a pusher-rotator.
Figure 3:
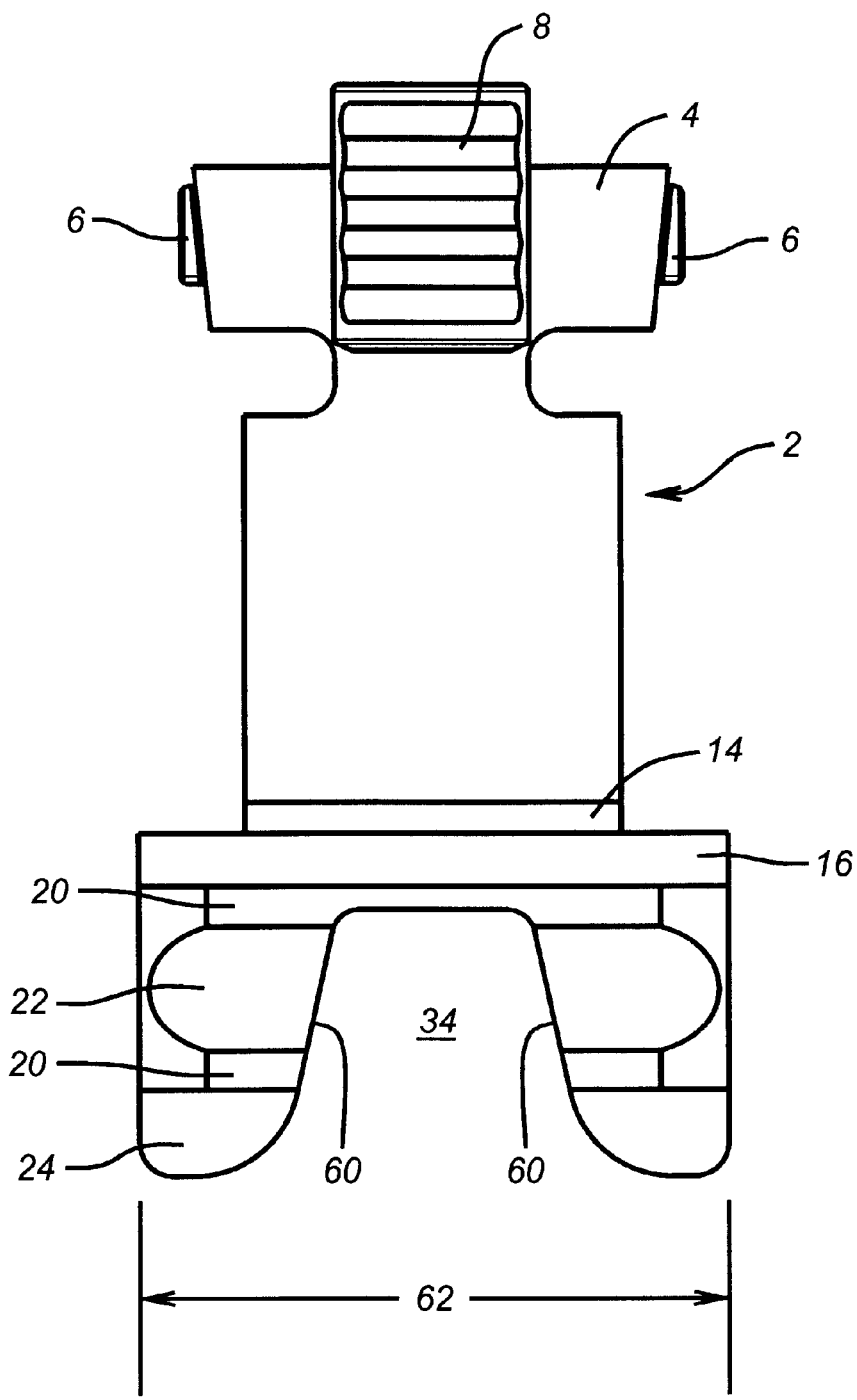
FIG. 3 is an end view of the pusher-rotator of FIG. 1.

Engaging end 4, FIGS. 1 and 2, includes a manually flexible release portion in the form of an annular ring 5 having an inner annular surface 5*a* which includes a pair of diametrically opposed flat engagement surfaces 5*b*. The finger tabs 8 are mounted diametrically opposed on an outer annular surface 5*c* of annular ring 5 in a cantilever manner. Finger tabs 8 include a gripping surface 8*a* for enhanced gripping. Finger tabs 8 are oriented at about 90° relative to flat surfaces 5*b*. A pair of radii 14 are provided so that the low profile pusher-rotator 2 is more easily cleaned.

Figure 4:
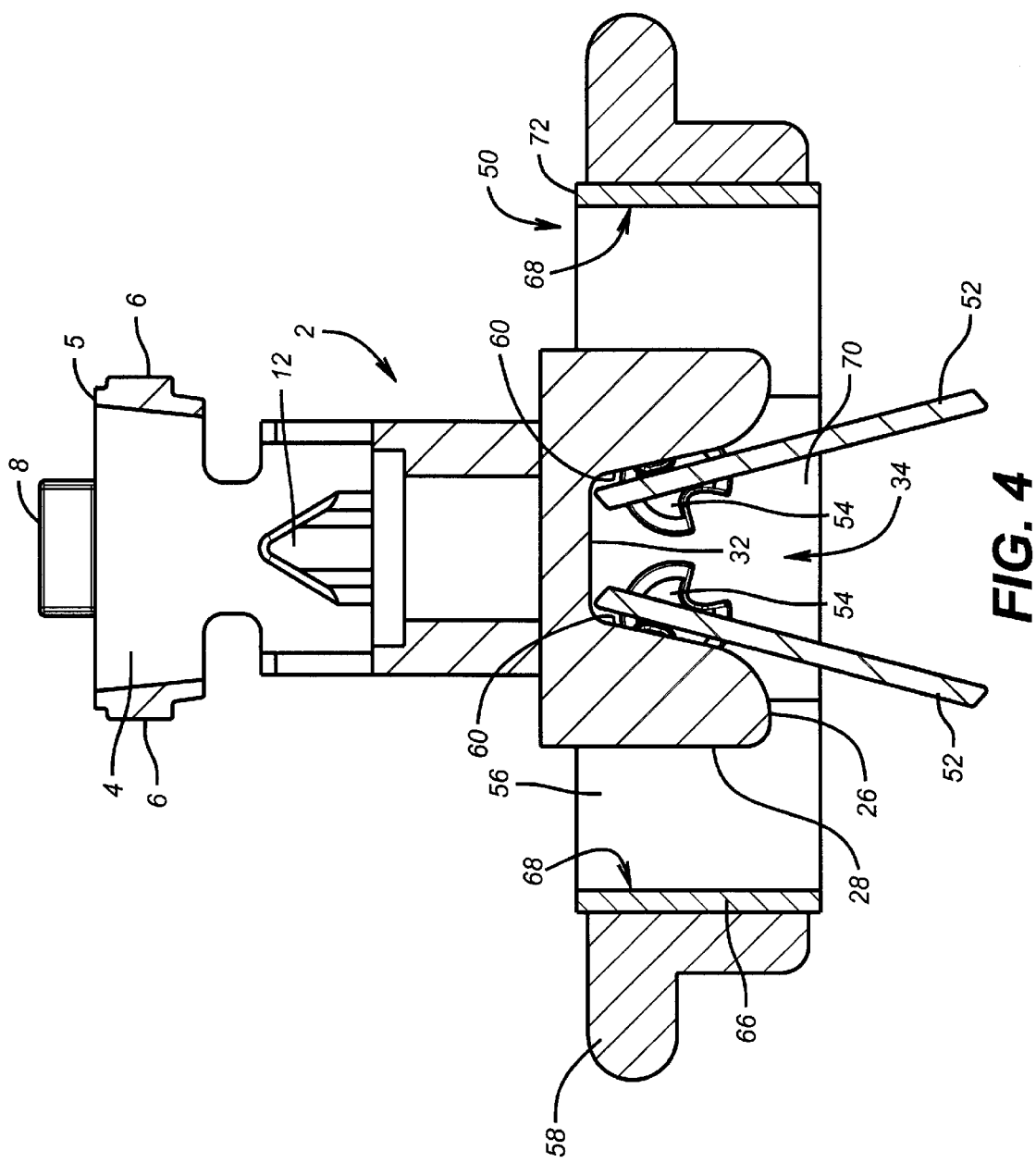
FIG. 4 is a cross-sectional side view illustrating an embodiment of a pusher-rotator engaged with a prosthetic heart valve.

Referring to FIG. 4, a heart valve prosthesis 50 is shown in cross-section, attached to pusher-rotator 2. The prosthesis 50 generally includes an annular valve body 66 with an interior surface 68. Surface 68 has a right circular cylindrical shape for a major portion of its length, but is interrupted by a pair of diametrically opposed flat sections 70 (as FIG. 4 is a cross-section, only one flat section 70 is shown). The distance between opposed flat sections 70 defines the smallest internal diameter of an annulus 56 of prosthesis 50. The annulus 56 is the central passageway through which blood flows, and contains a pair of leaflets 52 that swing or rotate about a pair of pivots 54. Pivots 54 reside in the flat sections 70 of prosthesis 50. Mounted around annulus 56 is a sewing ring 58 which provides means for the surgeon to attach prosthesis 50 to the patients natural valve annulus (discussed below).

As shown in FIG. 1, pusher-rotator 2 has a length 64 designed to fit between flat sections 70 when engaged with the prosthesis 50. This operative relation between length 64 and the inside diameter of annulus 56 allows the pusher-rotator 2 to position the prosthesis 50 while the leaflets 52 are protected.

In this particular embodiment, FIGS. 1–4, the low profile pusher-rotator 2 includes a series of coaxial cylinders which are truncated resulting in a width 62 small enough to pass through the intercostal spaces of the patient's ribcage, without significantly displacing any of the patient's ribs. In this embodiment, the width 62 of the cylinder is truncated to 14 millimeters. The restriction on width 62 always results in a low-profile pusher-rotator 2 with a length to width ratio of greater than 1. Of course, the ratio is not significant, so long as the width 62 is less than length 64, and therefore is less than the inside diameter of the prosthetic heart valve 50.

An outside cylinder 16 acts as a stop for the pusher-rotator 2 when it contacts an inflow edge 72 of the body 66, therefore, preventing the leaflets 52 from bearing any axial load. An engaging surface 18 of outside cylinder 16 is a surface that rests against the inflow edge 72 of the prosthetic heart valve 50 and provides for axial engagement. An engagement flat 20 is a surface that engages the flat portions 70 of the interior surface 68 of the prosthetic heart valve 50 and provides rotational force for positioning the valve 50. Flat 20 is formed from an intermediate cylinder 17, and induces the rotation of the valve 50. Flat 20 is formed by truncating cylinder 17 so that flat 20 occurs 90 degrees from the truncation at an intercostal release surface 28. The engagement flat 20 allows the pusher-rotator 2 to match the opposing flat surfaces 70 of the valve internal diameter.

A notch 22 is formed in cylinder 17 that aids in directing the pusher-rotator in the axial position. Notch 22 also helps guide the pusher-rotator 2 into correct alignment for full engagement with valve 50 when presented at an angle to the valves central axis. A cylinder formed at a surface 24 is slightly less than the distance between the orifice flats 70 and will engage the valve 50 for radial alignment. Cylinder surface 24 is smaller than the orifice flats 70 so the pusher-rotator 2 will be held in radial alignment with the valve 50 while it is rotationally being aligned. Cylinder surface 24 allows the pusher-rotator 2 to rotate freely on the leaflets 52 inflow edge which helps guide the pusher-rotator 2 into the correct rotational alignment for full engagement into the orifice and leaflets assembly. A pair of elongated surfaces 26 are also relieved to limit excessive pressure from being applied to the leaflets 52. A combination of surfaces 26, and a plurality of other surfaces 32 and 60 define a leaflet groove 34 and protect the leaflets 52 from rotational or axial pressure that may result in damage to the valve 50. Indeed, as shown in the embodiment in FIG. 4, groove 34 surrounds leaflets 52 while the leaflets 52 are in the open position, but does not exert pressure on, or necessarily touch the valve leaflets 52 during rotation of the valve 50. Intercostal release surface 28 provides the low profile character of pusher-rotator 2 so that it can be easily inserted between the patient's ribs. In the embodiment shown in FIG. 4, surfaces 60 are substantially parallel to leaflets 52 in the fully open position.

Figure 5:
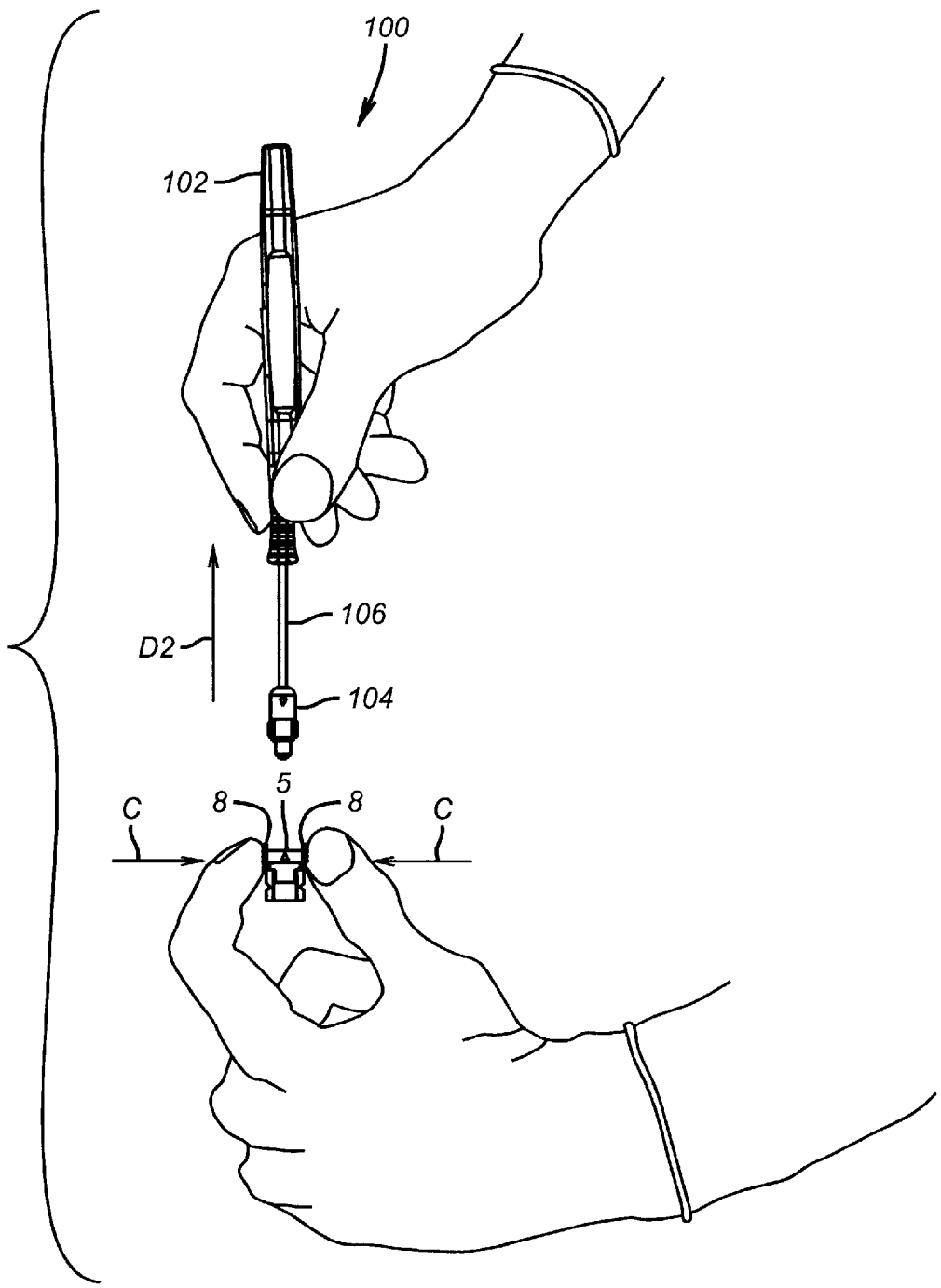
FIG. 5 is a side view illustrating an embodiment of a handle disconnected from a pusher-rotator.

The handle mentioned above is designated 100 in FIG. 5 and includes a first end 102, a second end 104 and a super-elastic shaft 106 interconnecting the first and second ends 102, 104, respectively. By super-elastic is meant a shaft 106 formed of nickel-titanium material such as Nitinol (R) SE and having the inherent ability to elastically deform to a very high strain and fully recover its original shape when the shaft ceases to be constrained. Second end 104, FIGS. 6 and 6b, includes a connector plug portion 108 having a longitudal axis designated P, and includes a pair of raised members 110 which are diametrically opposed and which include a pair of diametrically opposed axially extending slots 112 formed therein. Slots 112 are oriented at about 90 E relative to raised members 110. An alignment indicator 114 is also formed on plug portion 108. A seating annulus 116 forms a terminal end of plug portion 108. Manually flexing the finger tabs 8, FIGS. 1 and 5, toward each other in the direction indicated by arrows designated C, distorts annular ring 5 sufficient to move flat surfaces 5b away from one another in the direction indicated by arrows designated R.

In operation, referring to FIGS. 1–6b, plug portion 108 inserts into pusher-rotator 2 by movement of handle 100 toward pusher-rotator 2, in a direction D1, FIG. 6. Upon engagement of plug portion 108 and annular ring 5, raised members 110 engage flat surfaces 5b in a forced fit so that when seating annulus 116 seats in engagement recess 10 of pusher-rotator 2, flat surfaces 5b snap toward each other and engage raised members 110 for retaining plug portion 108 in pusher-rotator 2. Engagement of tabs 12 in slots 112 provides an anti-rotation connection between handle 110 and pusher-rotator 2. For separation of handle 100 from pusher-rotator 2, manual flexing of tabs 8 in the direction indicated by arrows C, FIGS. 1 and 5, distorts annular ring 5 sufficiently to move flat surfaces 5b away from each other in the direction indicated by arrows R, FIG. 1. This disengages flat surfaces 5b and raised members 110. Handle 100 can then be withdrawn in the direction indicated by the arrow designated D2, FIG. 5.

The super-elastic material used to form shaft 106, FIG. 7, permits easy flexure of shaft 106 from, for example, a first position P1, to a second position P2. This is advantageous because the pusher-rotator 2 is in fixed attachment with handle 100 such that pusher-rotator 2 does not articulate on the end of handle 100, see FIG. 6a. For simplicity of operation and cost-efficient manufacture, the connection between the handle 100 and pusher-rotator 2 is rigid; i.e., the pusher-rotator 2 cannot pivot or reorient relative to the second end 104 of the handle 100 for introduction through the intercostal space of a patient's ribs.

During a surgical procedure, valve 50 is sutured to a natural valve annulus 150, FIG. 8. Handle 100 and attached pusher-rotator 2 are easily inserted between a pair of adjacent ribs 155, FIG. 9, of a heart patient, and pusher-rotator 2 engages valve 50 in the manner described above. Valve 50 is then pushed in the direction indicated by the arrow designated X, FIG. 10, toward the natural valve annulus 150 and rotated as required, in the directions indicated by the arrow designated Y. Handle 100 and pusher-rotator 2 are then withdrawn from the valve 50 and are easily withdrawn between the adjacent ribs 155, as discussed above.

As it can be seen, the principal advantages of these embodiments is that attachment of the handle and the pusher-rotator is accomplished by a snap-on engagement and is also provided for quick release. The device easily engages a reusable endoscopic instrument, avoiding costly disposable valve handles such as those presently in use. The pusher-rotator easily passes through the common size 15 mm wide percutaneous intercostal incision avoiding the need to spread adjacent ribs apart. Parts are either machined or injection molded out of materials suited to the biomedical industry. Also, the device permits ease of engagement with a heart valve prosthesis for introduction into a natural valve annulus and subsequent rotation of the heart valve prosthesis for alignment of the valve orifice and leaflets without imposing damage on the leaflets.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A device for releasably holding and positioning a heart valve prosthesis comprising:
    a handle having a first end, a second end and a superelastic shaft interconnecting the first end with the second end;
    a connector at the second end of the handle, the connector including a connector portion; and
    a low profile pusher-rotator releasably engaged with the connector portion, the pusher-rotator including a manually flexible release portion having engagement surfaces engaged with the connector portion, said pusher-rotator having a generally rectangular configuration including a length and a width, wherein the rectangular configuration comprises parallel and flat surfaces extending substantially along the length, and other parallel and generally flat surfaces extending substantially along the width.

2. The device as defined in claim 1 wherein the release portion includes finger tabs adjacent the engagement surfaces.

3. The device as defined in claim 1 wherein the pusher-rotator includes guide tabs.

4. The device as defined in claim 3 wherein the connector portion includes guide slots engaged with the guide tabs.

5. The device as defined in claim 1 wherein the manually flexible release portion includes an annular ring.

6. The device as defined in claim 1 wherein the connector portion includes a first axis and the pusher-rotator includes a second axis aligned with the first axis.

7. The device as defined in claim 1 wherein the engagement surfaces are generally flat surfaces and snap into engagement with the connector portion, whereby manually flexing the release portion disengages the flat surfaces and the connector portion.

8. A device for holding and positioning a heart valve prosthesis having an annular configuration, the device comprising:
    a handle having a first end, a second end and a superelastic shaft interconnecting the first end and the second end;
    a connector at the second end of the handle, the connector including a plug portion having raised members;
    a pusher-rotator coupled to the connector and having a generally rectangular configuration including a length and a width, wherein the rectangular configuration comprises parallel and flat surfaces extending substantially along the length, and other parallel and generally flat surfaces extending substantially along the width; and
    a manually flexible release portion on the pusher-rotator including opposed engagement surfaces engaged with the raised members.

9. The device as defined in claim 8 wherein the release portion includes cantilever mounted opposed finger tabs adjacent the engagement surfaces.

10. The device as defined in claim 8 wherein the pusher-rotator includes axially extending opposed guide tabs.

11. The device as defined in claim 10 wherein the plug portion includes opposed axially extending guide slots engaged with the opposed guide tabs.

12. The device as defined in claim 9 wherein the manually flexible release portion includes an annular ring.

13. The device as defined in claim 8 wherein the plug portion includes a first axis and the pusher-rotator includes a second axis aligned with the first axis.

14. The device as defined in claim 12 wherein the engagement surfaces are generally flat surfaces and snap into engagement with the raised members, whereby manually flexing the finger tabs distorts the annular ring and disengages the flat surfaces and the raised members.

15. A device for holding a heart valve prosthesis having an annular configuration with an inside diameter, the device comprising:
    a handle having a first end, a second end and a superelastic shaft interconnecting the first end and the second end;
    a connector at the second end of the handle, the connector including a plug portion having a pair of raised members;
    a pusher-rotator coupled to the connector and having a length extending between the inside diameter of the heart valve, and a width, wherein the length is approximately equal to the inside diameter and the width is substantially less than the inside diameter, and wherein the pusher-rotator has a rectangular configuration, wherein parallel and flat surfaces extend substantially along the length and other parallel and generally flat surfaces extend substantially along the width; and
    a manually flexible release portion on the pusher-rotator including a pair of opposed engagement surfaces engaged with the raised members.

16. The device as defined in claim 15 wherein the release portion includes a pair of extended opposed finger tabs adjacent the engagement surfaces.

17. The device as defined in claim 15 wherein the pusher-rotator includes a pair of elongated opposed guide tabs.

18. The device as defined in claim 17 wherein the plug portion includes a pair of opposed elongated guide slots engaged with the opposed guide tabs.

19. The device as defined in claim 15 wherein the manually flexible release portion includes an annular ring.

20. The device as defined in claim 15 wherein the plug portion includes a first axis and the pusher-rotator includes a second axis aligned with the first axis.

21. The device as defined in claim 16 wherein the engagement surfaces are generally flat surfaces and snap into engagement with the raised members, whereby manually flexing the finger tabs disengages the flat surfaces and the raised members.

22. The device as defined in claim 15 wherein the width is about 14 mm.

23. The device as defined in claim 15 wherein the width is of a size sufficient to fit through an intercostal space between adjacent ribs of a patient.

* * * * *